United States Patent [19]
Asano et al.

[11] Patent Number: 5,965,557
[45] Date of Patent: Oct. 12, 1999

[54] METHOD FOR PROPHYLAXIS AND TREATMENT OF IRRITABLE BOWEL SYNDROME

[75] Inventors: Kiyoshi Asano; Shigemi Kino; Hiroshi Yasumatsu, all of Chikujo-gun, Japan

[73] Assignee: Yoshitomi Pharmaceuticals Industries, Ltd., Osaka, Japan

[21] Appl. No.: 09/167,566

[22] Filed: Oct. 7, 1998

[30] Foreign Application Priority Data

Nov. 10, 1997 [JP] Japan ................................. 9-307575

[51] Int. Cl.$^6$ ................................................ A61K 31/495
[52] U.S. Cl. ................................................ 514/248
[58] Field of Search .............................................. 514/248

[56] References Cited

U.S. PATENT DOCUMENTS 4,849,421   7/1989   Nakao et al. ............................. 514/248

FOREIGN PATENT DOCUMENTS 3-251586   11/1991   Japan .
5-55509    8/1993    Japan .

OTHER PUBLICATIONS

Pharmaceutical Daily, Oct. 8, 1997 issue, p. 2.
Pharmaceutical Daily, Oct. 27, 1997 issue, p. 4.

*Primary Examiner*—Raymond Henley, III
*Attorney, Agent, or Firm*—Wenderoth, Lind & Ponack L.L.P.

[57] ABSTRACT

A method for the prophylaxis and treatment of irritable bowel syndrome, which comprises administering a pharmaceutically effective amount of at least one compound selected from the group consisting of (±)-2-(4-chlorophenyl)-5,6-dihydro-[1]benzothiepino [5,4-c]pyridazin-3(2H)-one 7-oxide, optical isomers thereof and 2-(4-chlorophenyl)-5,6-dihydro-[1]benzothiepino[5,4-c]pyridazin-3(2H)-one 7,7-dioxide to a subject in need of such prophylaxis or treatment.

2 Claims, No Drawings

METHOD FOR PROPHYLAXIS AND TREATMENT OF IRRITABLE BOWEL SYNDROME

TECHNICAL FIELD OF THE INVENTION

The present invention relates to a method for the prophylaxis and treatment of irritable bowel syndrome.

BACKGROUND OF THE INVENTION

Japanese Patent Examined Publication No. 5-55509 discloses compounds, such as 2-(4-chlorophenyl)-5,6-dihydro-[1]benzothiepino[5,4-c]pyridazin-3(2H)-one 7-oxide, which have high affinity for a benzodiazepine receptor, which are highly safe, and which are useful as selective antianxiety drugs. These compounds are taught to be applicable for the prophylaxis, alleviation and treatment of autonomic imbalance, neurotic emesis, neurotic dermatitis, neurotic angina pectoris, neurotic respiratory distress and the like, as well as psychosomatic diseases and anxiety neurosis, such as anxiety and tension, which are induced by various diseases; useful as neutralizers of overdose and intoxication of existing antianxiety drugs such as diazepam; and useful as promoters of biophylaxis due to the pharmacological activity of the compounds, such as phylaxis and promotion of phagocytic activity of leukocyte and macrophage.

Incidentally, irritable bowel syndrome has been drawing attention as a disease presenting intestinal symptoms, such as altered bowel habits, abdominal pain, abdominal distension, abdominal dysphoria, borborygmus and the like, due to motility disorder and abnormal secretion of the colon, which are caused by dystonia of autonomic nervous system. These symptoms can be improved by normalizing the time of passage through the large intestine, and a medicament having a prokinetic activity has been used in clinical situations.

SUMMARY OF THE INVENTION

The present invention aims at providing a method for the prophylaxis and treatment of irritable bowel syndrome, particularly various symptoms of altered bowel habits, abdominal pain, abdominal distension, abdominal dysphoria, anorexia, borborygmus, emesis, belching, heartburn and the like.

The present invention is based on the finding that (±)-2-(4-chlorophenyl)-5,6-dihydro-[1]benzothiepino[5,4-c]pyridazin-3(2H)-one 7-oxide significantly suppresses the transit ability of the large intestine of experimental models, which had been promoted by the load of restraint stress. That is, the present invention relates to a method for the prophylaxis and treatment of irritable bowel syndrome, which comprises administering a pharmaceutically effective amount of at least one compound selected from the group consisting of (±)-2-(4-chlorophenyl)-5,6-dihydro-[1]benzothiepino[5,4-c]pyridazin-3(2H)-one 7-oxide, optical isomers thereof and 2-(4-chlorophenyl)-5,6-dihydro-[1]benzothiepino[5,4-c]pyridazin-3(2H)-one 7,7-dioxide, preferably (±)-2-(4-chlorophenyl)-5,6-dihydro-[1]benzothiepino [5,4-c]pyridazin-3(2H)-one 7-oxide, to a subject in need of said prophylaxis or treatment.

Inasmuch as the compound to be used in the present invention has suppressive activity against transit ability of the large intestine of an animal, it can be used also for the improvement of various symptoms associated with irritable bowel syndrome, such as altered bowel habits, abdominal pain, abdominal distension, abdominal dysphoria, anorexia, borborygmus, emesis, belching, heartburn and the like.

DESCRIPTION OF THE INVENTION

The compound to be used for the inventive method includes (±)-2-(4-chlorophenyl)-5,6-dihydro-[1]benzothiepino[5,4-c]pyridazin-3(2H)-one 7-oxide and optical isomers thereof, namely, R-(−)-2-(4-chlorophenyl)-5,6-dihydro-[1]benzothiepino[5,4-c]pyridazin-3(2H)-one 7-oxide, S-(+)-2-(4-chlorophenyl)-5,6-dihydro-[1]benzothiepino[5,4-c]pyridazin-3(2H)-one 7-oxide and 2-(4-chlorophenyl)-5,6-dihydro-[1]benzothiepino[5,4-c]pyridazin-3(2H)-one 7,7-dioxide. Of these compounds, (±)-2-(4-chlorophenyl)-5,6-dihydro-[1]benzothiepino [5,4-c]pyridazin-3(2H)-one 7-oxide is particularly preferable. In the present specification, (±)-2-(4-chlorophenyl)-5,6-dihydro-[1]benzothiepino[5,4-c]pyridazin-3(2H)-one 7-oxide may be sometimes referred to as Y-23684. These compounds can be synthesized according to the method disclosed in Japanese Patent Examined Publication No. 5-55509 and Japanese Patent Unexamined Publication No. 3-251586.

The inventive medicament for the prophylaxis and treatment is formulated in a dosage form suitable for oral, parenteral or rectal administration. The dosage form of the pharmaceutical preparation includes tablet, capsule, troche, syrup, granule, powder, injection, suspension, suppository and the like. It can be prepared into two-layer tablet or multilayer tablet with other drugs. The tablets can be made into those having usual film coating as necessary, such as sugar-coated tablets, enteric coated tablets and film coated tablets.

When preparing a solid preparation, additives such as lactose, sucrose, crystalline cellulose, corn starch, calcium phosphate, sorbitol, glycine, carboxymethylcellulose, gum arabic, polyvinylpyrrolidone, hydroxypropylcellulose, hydroxypropylmethylcellulose, glycerol, polyethylene glycol, magnesium stearate, talc and the like are used.

When preparing a semisolid preparation, fats and oils from animals and plants, such as olive oil, corn oil, castor oil and the like; mineral fats and oils such as petrolatum, white petrolatum, solid paraffin and the like; wax such as jojoba oil, carnauba wax, beeswax and the like; and partially or entirely synthesized glycerine fatty acid esters, such as lauric acid, myristic acid, palmitic acid and the like, are used. Examples of commercially available products of these include Witepsol (manufactured by Dynamitnovel Ltd.), Pharmasol (manufactured by NOF Corporation) and the like.

When preparing a liquid preparation, additives such as sodium chloride, sorbitol, glycerol, olive oil, propylene glycol, ethyl alcohol and the like are used.

Moreover, oral preparations can be produced using a pulverization mixture as disclosed in Japanese Patent Examined Publication No. 8–18985.

These preparations contain an active ingredient in a proportion of 0.1–100 wt % of the preparation, wherein it is generally 1–50 wt % for oral preparations and 0.2–20 wt % for injections.

The subject is free of any particular limitation as long as the subject is suffering from irritable bowel syndrome or has a potential of developing irritable bowel syndrome in the future, with preference given to a mammal, particularly human.

While the dose varies depending on the symptom, body weight, age and the like of the subject, it is, in general, approximately 0.01–100 mg, preferably 0.03–60 mg, and particularly preferably 2–8 mg, daily for an adult by oral administration in a single dose or several doses.

The formulation examples of the prophylactic and therapeutic medicament of the present invention are shown in the following, which are not to be construed as limiting the invention.

Formulation Example 1

| | |
|---|---|
| Y-23684 | 10.0 mg |
| Lactose | 30.0 mg |
| Corn Starch | 19.8 mg |
| Crystalline cellulose | 28.0 mg |
| Talc | 2.0 mg |
| Magnesium stearate | 0.2 mg |
| Hydroxypropylmethylcellulose | 4.0 mg |
| Titanium oxide | 1.0 mg |
| Total amount | 95.0 mg |

Y-23684, lactose, corn starch and crystalline cellulose are mixed and a part of corn starch is kneaded in as a paste to give granulates, which is followed by drying at 50° C. for 3 hr. The dried granules are passed through a 24-mesh sieve, and talc and magnesium stearate are added. Using a 6.0 mm diameter pounder and a rotary tableting machine, tablets weighing 90 mg per tablet are produced. Then, a coating comprising hydroxypropylmethylcellulose and titanium oxide as film coating bases is applied at 5 mg per tablet.

Formulation Example 2

| | |
|---|---|
| Y-23684 | 10.0 mg |
| Cornstarch | 20.0 mg |
| Lactose | 81.5 mg |
| Crystalline cellulose | 30.0 mg |
| Hydroxypropylcellulose | 3.0 mg |
| Talc | 5.0 mg |
| Magnesium stearate | 0.5 mg |
| Total amount | 150.0 mg |

Y-23684 and corn starch are vigorously mixed in a dry state in a mortar to give a pulverization mixture. The obtained powder mixture, lactose and crystalline cellulose are thoroughly mixed in a kneader. A hydroxypropylcellulose paste solution is added and the mixture is kneaded to give granules. The granules are passed through a 16-mesh sieve and dried in a hot air dryer at 50° C. to the water content of 3–4%. The resulting product is passed through a 24-mesh sieve, and talc and magnesium stearate are added. Using a 7.5 mm diameter pounder and a rotary tableting machine, tablets weighing 150 mg per tablet are produced.

Formulation Example 3

| | |
|---|---|
| Y-23684 | 0.3 g |
| Witepsol H15 | 35.7 g |
| Total amount | 36.0 g |

Witepsol H15 (35.7 g) is melted at approximately 40° C. and the active ingredient Y-23684 (0.3 g) is added, which is followed by stirring for dispersion. The resulting uniform mixture is packed in a suppository mold so that each suppository weighs 1.2 g, whereby suppositories containing 10 mg of Y-23684 in one suppository (1.2 g) are produced.

The pharmacological effect of Y-23684 was demonstrated by investigating its effect on large intestinal transit in rats.

EXPERIMENTAL EXAMPLE 1

Effect On Large Intestinal Transit Under Restraint Stress

A silicon tube was inserted in the caecum of wistar rats (14–17 rats per group) and the test drug was orally administered. Thirty minutes later, an Evans blue solution (0.4 ml, 25 mg/ml) was injected into the caecum. The rats were placed in a restraining cage, and the caecum and colon were removed 45 minutes later. The proportion of the length from the origin to the stained end of the colon to the entire length of the colon was calculated and taken as a transit ratio. For comparison, diazepam (30 mg/kg) was administered in the same manner and the transit ratio was calculated. The group free of drug administration was used as a control. The results are shown in Table 1.

TABLE 1

| Test drug | Dose (mg/kg) | Transit (%) |
|---|---|---|
| control | | 79.3 |
| Y-23684 | 3 | 72.2 |
| control | | 87.4 |
| Y-23684 | 10 | 57.9** |
| control | | 79.3 |
| Y-23684 | 30 | 58.2* |
| control | | 79.3 |
| diazepam | 30 | 68.2 |

In the Table, * means a significance level of not more than 0.05%, and ** means a significance level of not more than 0.01%.

From the results shown in Table 1, it is evident that Y-23684 at the dose of 10 and 30 mg/kg by oral administration significantly suppressed the large intestinal transit ability promoted by the restraint stress load. In contrast, diazepam did not show any significant effect even at the dose of 30 mg/kg.

As shown in the above-mentioned Experimental Example, it has been demonstrated that the present compound is effective for the prophylaxis and treatment of irritable bowel syndrome associated with various symptoms caused by motility disorder of the large intestine, such as altered bowel habits.

This application is based on application No. 307575/1997 filed in Japan, the content of which is incorporated hereinto by reference.

All publications mentioned in this specification inclusive of patents and patent applications are herein incorporated by reference.

What is claimed is:

1. A method for the prophylaxis or treatment of irritable bowel syndrome, which comprises administering a pharmaceutically effective amount of at least one compound selected from the group consisting of (±)-2-(4-chlorophenyl)-5,6-dihydro-[1]benzothiepino[5,4-c]pyridazin-3(2H)-one 7-oxide, optical isomers thereof and 2-(4-chlorophenyl)-5,6-dihydro-[1]benzothiepino[5,4-c]pyridazin-3(2H)-one 7,7-dioxide to a subject in need of said prophylaxis or treatment.

2. The method for the prophylaxis or treatment of irritable bowel syndrome according to claim 1, wherein said compound is (±)-2-(4-chlorophenyl)-5,6-dihydro-[1]benzothiepino[5,4-c]pyridazin-3(2H)-one 7-oxide.

* * * * *

UNITED STATES PATENT AND TRADEMARK OFFICE
CERTIFICATE OF CORRECTION

PATENT NO. : 5,965,557
DATED : October 12, 1999
INVENTOR(S) : Kiyoshi Asano, et. al.

It is certified that error appears in the above-identified patent and that said Letters Patent is hereby corrected as shown below:

Title page, item [73], Assignee: should read as following: --
Yoshitomi Pharmaceutical Industries, Ltd.--

Signed and Sealed this

Twenty-sixth Day of December, 2000

Attest:

Q. TODD DICKINSON

*Attesting Officer*  *Director of Patents and Trademarks*